United States Patent
Malessa et al.

(10) Patent No.: US 9,023,369 B2
(45) Date of Patent: May 5, 2015

(54) FREEZE-DRIED COMPOSITION OF ACTIVE SUBSTANCES

(76) Inventors: Ralf Malessa, Essen (DE); Claudia Elsinghorst, Billerbeck (DE); Fabian Kuhlmann, Rosendahl (DE); Uwe Wagner, Senden (DE)

(*) Notice: Subject to any disclaimer, the term of this patent is extended or adjusted under 35 U.S.C. 154(b) by 274 days.

(21) Appl. No.: 12/763,605

(22) Filed: Apr. 20, 2010

(65) Prior Publication Data

US 2010/0273747 A1    Oct. 28, 2010

(30) Foreign Application Priority Data

Apr. 22, 2009    (EP) .................................... 09158473

(51) Int. Cl.

| | | |
|---|---|---|
| *A61K 31/60* | (2006.01) | |
| *A61K 31/34* | (2006.01) | |
| *A61K 47/10* | (2006.01) | |
| *A61K 9/19* | (2006.01) | |
| *A61K 8/368* | (2006.01) | |
| *A61K 8/67* | (2006.01) | |
| *A61K 8/73* | (2006.01) | |
| *A61Q 19/00* | (2006.01) | |

(52) U.S. Cl.
CPC . *A61K 9/19* (2013.01); *A61K 8/368* (2013.01); *A61K 8/676* (2013.01); *A61K 8/733* (2013.01); *A61K 2800/84* (2013.01); *A61Q 19/00* (2013.01)

(58) Field of Classification Search
CPC . A61K 2300/00; A61K 9/19; A61K 2800/84; A61K 31/375; A61K 31/722; A61K 8/676; A61K 9/205; A61K 47/26; A61K 8/733
USPC .......................... 424/400; 514/159, 165, 474
See application file for complete search history.

(56) References Cited

U.S. PATENT DOCUMENTS

| | | | |
|---|---|---|---|
| 2006/0024370 A1* | 2/2006 | Nguyen et al. ................. 424/484 |
| 2008/0305160 A1 | 12/2008 | Guimberteau et al. | |
| 2010/0226982 A1* | 9/2010 | Malessa ......................... 424/484 |
| 2010/0272762 A1* | 10/2010 | Malessa et al. ................ 424/400 |
| 2010/0272834 A1* | 10/2010 | Malessa ......................... 424/729 |

FOREIGN PATENT DOCUMENTS

| | | | | |
|---|---|---|---|---|
| CN | 101094658 A | 12/2007 | | |
| DE | 102006038629 | 2/2008 | | |
| DE | 102006038629 A1 * | 2/2008 | ............... | A61K 8/00 |
| EP | 888769 | 1/1999 | | |
| FR | 2886845 | 12/2006 | | |
| WO | 01/28600 | 4/2001 | | |
| WO | 03/068843 | 8/2003 | | |
| WO | 2004035023 | 4/2004 | | |
| WO | 2008/020066 | 2/2008 | | |

* cited by examiner

*Primary Examiner* — Aradhana Sasan
(74) *Attorney, Agent, or Firm* — Fanelli Haag PLLC

(57) ABSTRACT

The invention relates to freeze-dried molded articles, containing ≥50% by wt. of one or more active substances, and ≤15% by wt. of one or more scaffold-forming agents, with proteins being excepted, as well as optionally one or more auxiliary substances, in each case based on the total composition of the freeze-dried molded article, whose 1% by wt. solution or suspension in water, at 20° C., has a pH value <7. Furthermore, the invention relates to methods for manufacturing these freeze-dried molded articles, the combination of such freeze-dried molded articles in kit-of-parts arrangements together with aqueous solutions, as well as the use of the freeze-dried molded articles and the kit-of-parts combinations for pharmaceutical and cosmetic application.

12 Claims, No Drawings

FREEZE-DRIED COMPOSITION OF ACTIVE SUBSTANCES

BACKGROUND OF THE INVENTION

The invention relates to freeze-dried molded articles, containing ≥50% by wt. of one or more active substances, and ≤15% by wt. of one or more scaffold-forming agents, with proteins being excepted, as well as optionally one or more auxiliary substances, in each case based on the total composition of the freeze-dried molded article, the 1% by wt. solution or suspension in water, at 20° C., has a pH value <7.

Furthermore, the invention relates to methods for manufacturing these freeze-dried molded articles, the combination of such freeze-dried molded articles in kit-of-parts arrangements together with aqueous solutions, as well as the use of the freeze-dried molded articles and the kit-of-parts combinations for pharmaceutical and cosmetic application.

A number of important and highly potent active substances for cosmetic and pharmaceutical application is known for being unstable and for being altered or decomposed, due to external influences, in such a way that they are no longer or no longer sufficiently capable of having the desired action in the composition in which they are contained, or that the altered active substances or their decomposed by-products even develop a harmful action. Among such unstable active substances, in particular such active substances must be mentioned in this respect which have a high degree of instability under thermal influences, as well as those that are highly susceptible to light, moisture and/or oxidation.

There is therefore a central interest in bringing such highly potent and highly unstable active substances, which are in danger of being decomposed, into a form which affords high and long-term stability, accompanied by good storability, optimal and reproducible provision of the content of active substances over the entire storage and administration period, and thus the highest possible safety and efficiency in application.

Apart from an effective stabilization of the active substances, in this context, their provision in an optimally suitable form of administration that is optimally adapted to the respective purpose of application is of particular interest. The choice of the suitable form of application in this case particularly depends on the type and place of application, the target group and its special characteristics, the type and quantity of the dosage of the active substances or their form of application, as well as, for example, the physical and biochemical characteristics of the active substances, in particular with regard to their biological availability and their systemic mode of action, which must be taken into consideration in this case.

Especially forms of application for external application as well as oral forms of application are of particular interest for providing such stable highly potent active substances in this case. In this context, in particular such forms of administration are particularly suitable and preferred for such applications, which can be used in aqueous and/or water-containing formulations or environments, and which are rapidly soluble in such aqueous environments. This is of importance in particular in the case of systems of active substances for oral application.

In order to protect biological or substances against moisture-related decomposition, deterioration or degradation, the method of freeze drying is known and widely used. In this case, the substance are frequently directly subjected to freeze drying, and the unstable active substances as such are preserved in particular in pharmaceutics. With regard to the provision of the freeze-dried, preserved active substances in suitable pharmaceutical or also cosmetic forms of application for finally applying them to or in the body, however, the problem arises of incorporating the freeze-dried and thus stabilized active substances in a stable and thus moisture-protected manner into the desired form of administration. Dry forms of application, such as powder mixtures, mixtures pressed into tablets, active substances filled into capsules or systems of active substances processed into granules are well-known. The drawbacks such application systems entail are in particular the frequently poor solubility and thus slow active substance release, the high proportion of auxiliary and filler substances, which are inactive but necessary for processing, the regularly poor suitability for external application as well as an insufficient dosability and thus unsafe handling or problems with application by the user.

A suitable and known manner of providing active substances in a form of application or dosage is to disperse the active substances in a system of carrier substances and to subject this mixture to freeze drying. Mostly, such substances are selected as carrier substances that have a good dissolution or swelling behavior and which, through swelling, enable a good texture formation, so that the dissolved active substance system, or the active substance system dispersed in the swelling agent, can be used directly as a form of application. Such systems, because of their good solubility, are known and suitable for providing oral forms of application, as well as for producing cosmetic or pharmaceutical forms of administration for external application. In this case, there in a increasing interest in providing so-called single-unit forms of application which enable a simple and precise application of a dose of an active substance for the end user. Single-unit forms of application in this context are understood to be application systems, which in contrast to powders or granules contain the desired and required quantity of active substance per application unit in a single application unit, such as tablets or capsules, without, however, having the drawbacks of poor solubility or lack of suitability for external application.

Thus, such easily soluble single-unit forms of application, which are moisture-stabilized by drying, for oral and/or external application of unstable active substances are becoming increasingly interesting in the form of larger-format embodiments, in particular if large quantities of active substances are to be administered. As a rule, the special challenge in this respect lies in providing high contents of active substances in a rapidly soluble form, and one that is soluble as completely or free of residues as possible, with as high an active substance content as possible, at as small a proportion of carrier or auxiliary substances in the composition as possible being desirable. The smaller the content in carrier or auxiliary substances, the more residue-free and more complete, as a rule, dissolution is, the smaller, however, the mechanical stability of the single molds is, as a rule, which plays a role in packaging, storing and handling in particular of large-format molded articles.

The swellable or soluble carrier substances commonly used in such forms of application are mostly selected from carrier substances which have particularly good swelling and dissolving properties in a neutral to alkaline environment, that can therefore be processed particularly well in this pH range. Moreover, for formulations to be applied externally, neutral to slightly alkaline formulations are commonly used, because those generally have a better skin compatibility and exhibit less irritation tendency. Especially for the group of acid active substances, i.e. such active substances that have a pH-dependent dissociation tendency and are therefore present in a dissociated form under neutralized or alkaline conditions, however, the problem arises that such systems can only be subjected to freeze drying in a limited extent, in particular at high contents of active substances. On the one hand, because of the high dissociation tendency of such active substances, such a high ion concentration develops in the formulation to be freeze-dried that a lowering of the freezing point of the composition occurs which renders the conditions for freeze drying unacceptably difficult. Moreover, the high ion concentration in the freeze-dried product increases its hygroscopicity to such a degree that in particular formulations with low contents of carrier substances, which have a decisive influence on the mechanical stability of the freeze-dried compositions, are not sufficiently stable. Known and important acid active substances that have the aforementioned properties, are, for example, ascorbic acid (vitamin C) and its derivatives, as well as, for example, acetylsalicylic acid (ASS) an its derivatives.

Thus, there is the necessity of providing large-format single-unit forms of application that can be dosed well, which have a high load of unstable, in particular acid active substances with a high, pH-value dependent dissociation tendency and a low content of insoluble or swellable carrier substance, and thus rapid and complete solubility and the highest possible mechanical stability for cosmetic and pharmaceutical external and oral use.

Dosable, active-substance charged pellets or single-unit drug forms of a certain size, which are supposed to make the provision of hydrolysis-sensitive active substances, such as vitamins, in particular vitamin C possible for both pharmaceutical as well as cosmetic application, are described in U.S. Pat. No. 5,405,618 and in DE4201179. The carrier materials used therein preferably are based on proteins. The pellets are produced by dripping dispersions of the protein scaffold-forming agents and optionally cosmetic or pharmaceutical active substances into cryogenic inert liquids, preferably liquid nitrogen, and subsequently separating and freeze-drying the frozen pellets. However, the presence of protein scaffold-forming agents, in particular of collagen or collagen derivatives, is necessary in order to form pellets under these conditions, because only the aforementioned protein scaffold-forming agents are able to form stable pellets under these conditions. Moreover, it is not possible to produce such molded articles with the production process described herein that have a high content of active substances and only a low content of scaffold-forming agents. Though the described method is described to be particularly suitable particularly for making hydrolysis-sensitive active substances, such as ascorbic acid (vitamin C) or acetylsalicylic acid available, however, the compositions described in the examples are all characterized by the content of scaffold-forming constituents being several times higher than the content of active substances. Thus, the method is not suitable for providing pellets with concentrations of active substances that are particularly high compared with the scaffold-forming carrier material. This is also connected with the special requirements with regard to a high-level stabilization of the composition in the dripping method used.

Similar problems result from the method for producing porous galenic particles described in U.S. Pat. No. 5,843,347, which are supposed to be obtained in sizes of up to 5 mm, according to the description. In the method used herein, a mixture of the active substances is extruded in a matrix and cut into particles with the desired size, which subsequently form the porous molded articles by freeze drying. However, the exemplary embodiments merely show that so-called microspheres with diameters of up to a maximum of 1.5 mm can be obtained. This can be ascribed to the use according to the invention of an extrusion and cutting method that requires a certain mechanical stability of the extruded mass. This can generally be obtained by a relatively high content of scaffold-forming polymers or carrier substances and stabilizers or fillers. However, if only small amounts of stabilizing carrier or auxiliary substances are used as compared with the content of active substances, then only very small-format microspheres can be obtained, as is shown in this document. The subject matter of the disclosure does not include any special possibility of stabilizing unstable, in particular so-called acid active substances.

Another method comprising the production of an emulsion containing the active substances, pouring said emulsion into a mold, and subsequent freeze drying of the emulsion, is the subject matter of WO 05/073296. According to the statements in the descriptive part, the molded articles that can be produced with this method can be obtained in sizes of 0.2-5 mm and larger, are soluble or dispersible in water, and this method is also supposed to provide a possibility of stabilizing unstable active substances, such as vitamins. However, the subject matter of the present method primarily is providing molded articles, into which the active substances are incorporated in an oil-in-wafer emulsion which additionally comprises emulsifiers, such as surfactants, in order to prepare this emulsion. However, this method also shows that the incorporation of extremely high contents of active substances at low quantities of scaffold-forming agents is not possible for reasons of stability of the large-format molded articles. Thus, the content of the scaffold-forming agents is specified to be 10 to 95% at a surfactant content of up to 5%. The example also does not offer any suggestions that the method described is suitable for producing molded articles consisting primarily of a moisture-stable, in particular acid active substance with only small amounts of stabilizing polymer. Document JP 2004-148468 describes a method for stabilizing a moisture-unstable active substance, L-ascorbic acid-2-phosphate, an ascorbic acid derivative (vitamin C derivative) by freeze drying an active substance-scaffold-forming agent-mixture while obtaining a readily soluble freeze-dried molded articles for cosmetic treatment. In this method, however, the stabilization of the active substance is achieved by using a very specific combination of scaffold-forming agents consisting of an oligosaccharide, sugar alcohol and a water-soluble polymer in specific quantity ratios. The quantity ratios show that also in this case, only such freeze-dried molded articles loaded with active substances are obtained in which the content of the stabilizing scaffold-forming agent by far exceed the content of active substances.

For both cosmetic and pharmaceutical application of single-application molded articles, relatively large molded articles of a uniform shape and size are preferred because in contrast to powders or small pellets, microspheres and granules, they can be handled more easily by the end user, so that the intention is to provide molded articles of such a size that permit a single dosage form per application. Moreover, larger molded articles, which can, for example, be given a colored design, also leave a stronger aesthetic impression.

In this context, the use of protein scaffold-forming agents is not preferred in some cases. Thus, some final increasingly prefer the use of pure plant products, in particular in cosmetics. The reasons for this result, among other things, from basic ethical considerations.

The processing of proteins moreover generally requires complicated processing and purification steps. Furthermore, the properties of the protein scaffold-forming agents in the external application on the skin are too limited with regard to their range of properties, because they are always composed of the same amino acids.

In order to obtain rapidly soluble large-format molded articles that are as completely soluble as possible with a high load of active substances as desired both in cosmetics as well as in pharmaceutical use, which in particular make the stable provision of moisture-sensitive and in particular so-called acid active substances possible, such as, for example, ascorbic acid (vitamin C) and its derivatives, or acetylsalicylic acid and its derivatives, such scaffold-forming agents of non-proteinogenic origin, such as in particular plant polymer scaffold-forming agent such as high-molecular polysaccharides, e.g. alginates or animal polyaminosaccharides, such as chitin and its derivatives, in particular chitosan, for the aforementioned reasons, are thus particularly suitable for producing such freeze-dried active-substance molded articles, also because of their solution behavior and their high gel forming capacity.

Thus, DE 10248314, which was also published as WO 2004/035023, describes large-formal molded articles of a regular shape loaded with active substances, which articles can be obtained by a freeze-drying method of an active substance-scaffold-forming agent-mixture poured into molds. The molded articles that can be obtained according to the described method are characterized by good mechanical stability and a high dissolution rate. The molded articles described can be obtained with quantities of plant scaffold-forming agents of at least 10% by wt. based on the total composition. Though amounts of 0-85% by wt. are in principle specified as possible contents of active substances, it is emphasized that loads of active substances ≤50% by wt. are being preferred. Only embodiments with up to a maximum of 25% by wt of active substance (example 4) are supported by the examples. Moreover, no suggestions are given by the document as regards a specific pH value of the molded articles disclosed therein, such as in particular a pH value <7 or even ≤6 or ≤4. Numerous groups and classes of active substances are being listed as possible active substances. No special focus on the stabilization of unstable active substances, in particular those that have a low moisture stability and a high dissociation tendency in a neutral to alkaline environment (so-called acid active substances) can be seen in this document, nor is a suggestion with regard to a stabilization of such unstable acid active substances by means of a specific pH value setting apparent. The dissolution rate of the molded articles described lies in a range of <4 minutes; it is dependent in principle on the respective content of scaffold-forming agents.

Fundamentally, such preparations having a particularly low content of scaffold-forming agents are more rapidly and completely soluble than those having a high content of scaffold-forming agents. In the case of especially large-format molded articles, in particular those based on plant scaffold-forming agents, such as alginates, and their use in a very small ratio relative to the active substance present, the problem quickly arises of obtaining sufficient mechanical stability in order to be able to produced molded articles with a regular form and rapid and complete solubility as they are required both for external applications as well as for oral application.

In particular the incorporation and stabilization of large quantities of such moisture-labile, acid active substances, such as ascorbic acid (vitamin C) and its derivatives or acetylsalicylic acid and its derivatives, which, besides their high moisture susceptibility, also have the effect of lowering the freezing point because of their dissociation tendency, is so far not possible in freeze-dried compositions, such as in the scaffold-forming agent-containing freeze-dried molded articles disclosed in DE 10248314. Due to the freezing-point lowering effect of such dissociated active substances large ice crystals with a large content of non-freezable water and high active substance concentrations or ion concentrations form in the frozen molded article, which lead to a partial structural collapse of the freeze-dried final product, to a so-called thawing of the molded article, so that the production of mechanically stable, uniform and attractive molded articles could so far not be carried out with the methods described.

DE 2017373 solves the problem of thawing of high quantifies of freezing-point lowering vitamin C in the production of mechanically stable, rapidly and completely soluble, moisture-stable, dosable pharmaceutical single-application forms by the content of freezing-point lowering vitamin C, which at approximately 30% by wt. is already unusually high, being mixed together with a quantity of approximately 70% by wt. of scaffold-forming agent and proteinogenic filler glycine after the vitamin C has previously been foamed with a synthetic block copolymer.

The use of such synthetic block copolymers, however, is not desired in cosmetic and pharmaceutical preparations because in principle, the use of synthetic substances or of carrier, auxiliary or additive substances without an actual pharmacological effect is to be kept at a minimum in order to avoid possible toxicological or pharmacological side effects. Furthermore, the addition of polymer carrier substances in principle reduce the solubility of the preparations as their content increases, which is why it is desirable to work with as small amounts as possible and to use, if possible, natural and toxicologically harmless polymer and carrier substances.

Therefore, the object of the present invention lay in providing a freeze-dried composition in which extremely high amounts of unstable, even so-called acid active substances (substances having a pKa value ≤7 at 25° C.) could be kept stabilized long-term and which could be released and applied rapidly, efficiently, specifically and highly actively during application. Moreover, another object lay in finding for these freeze-dried compositions a possibility of incorporating large quantities of such acid active substances, which in principle have a freezing-point lowering effect and which thus could not be used for the production of freeze-dried preparations so far. Moreover, the object lay in designing these stable active substance compositions in such a way that they have high mechanical strength and sufficient size in order, in particular, to be capable of being used for cosmetic or pharmaceutical application in the form of so-called single-dose units or single-dosage applications. In this case, the compositions are supposed to be equally suited for external application as well as for an oral or peroral application.

Surprisingly, it was found that, based on the above-mentioned DE 10248314 (WO 2004/035023), such stable, large-format active substance-loaded molded articles could be produced that contain quantities of active substances, which at ≥50% by wt. content of active substances and ≤15% by wt. content of scaffold-forming agents, lie in the outermost limits of DE 10248314, and in particular beyond them. Surprisingly, in particular unstable, acid active substances which, due to their freezing-point lowering effect, could not be worked into freeze-dried compositions of the present type in such large quantifies so far, can be incorporated in this case by the compositions into which the active substances are incorporated being previously adjusted to a pH value ≤7, preferably ≤6, more preferably ≤5, particularly preferably ≤4.

Freeze-dried compositions containing at least 10% by wt. of carrier materials as well as up to 50% by wt. active substances in stabilized form, preferably in the form of derivatives and/or precursors of active substances, are known from DE 102006038629. As active substances, those from the group of vitamins, such as in particular vitamin C (ascorbic acid) and derivatives are specified as being particularly preferred in this case. Moreover, the compositions contain up to 50% by wt. of an agent for forming the active substance from the stabilized form upon addition of an aqueous phase to the composition. Such releasing agents are preferably selected from the group of enzymes. However, DE 102006038629 does not offer any suggestions as to a specific pH value of the molded articles disclosed therein, such as, in particular, a pH value of <7 or even ≤6 or ≤4. Only in connection with the preferably used carrier materials from the group of the alginates is a preferred pH value of 6-8 mentioned. However, the latter only serves for characterizing the alginates used and does not make if possible to draw any conclusion as to the pH value for the molded article according to the invention that is obtained in the end.

The corresponding international application WO 2008/020066 goes beyond the disclosure of the above-mentioned DE 102006038629 in that it additionally contains the exemplary embodiments 1 to 5. In this case, examples 1 to 3 disclose the production of an appropriate freeze-dried composition, wherein the pH value is adjusted to 4-5 and wherein the obtainable compositions comprise approx. 16% by wt. carrier material and approx. 1.6% by wt. stabilized active substance (ascorbyl glucoside). In addition, approximately 82% by wt. of the enzyme glucoamylase is added to the compositions in the form of a commercially available enzyme solution (Novozym 300 GL; 10-40%) as well as, optionally, further auxiliary substances. The commercially available enzyme solution Novozym 300 GL contains 10 to 40% glucoamylase, whereby the latter can be contained in the composition in a proportion of approximately 8 to maximally 33% by wt.

Though in principle, enzymes can also develop activity as an active substance, however, in the present case enzymes are not included in the definition of the active substances which are present in particular in the form of stabilized derivatives. Glucoamylase is added to the compositions merely as a releasing agent which releases the active substance ascorbic acid upon addition of a liquid. Furthermore, a content of active substances ≥50% by wt. is not disclosed in any case by the examples 1-3 of WO 2008/020066, even taking into account the enzymes. Thus, documents DE 102006038629 and WO 2008/020066 do not disclose any freeze-dried compositions with a content of active substances ≥50 by wt. and a pH value <7 or even ≤6 or ≤4.

From FR 2 886 845, furthermore, dry compositions are known which may contain scaffold-forming agent, such as sodium alginates, in an amount of 15-75% by wt., as well as ascorbic acid in a content of 0.1-80% by wt., and which can be obtained, inter alia, by lyophilization. However, this document does not offer any concrete suggestions as to a pH value to be selected specifically, especially as the object of stabilization of the unstable active substance ascorbic acid is achieved by FR 2886845 by adding the maleic acid copolymer. Thus, this document also does not offer any suggestions as to a freeze-dried composition with a content of active substances ≥50% by wt. and a specific pH value <7 or even ≤6 or ≤4. A concrete pH value is merely specified in connection with the exemplary embodiment 1, with the composition disclosed therein not disclosing any particularly high contents of active substances ≥50% by wt. Thus, freeze-dried molded articles with a content of active substances ≥50% by wt. and a specific pH value <7 or even ≤6 or ≤4 are also not apparent from FR 2 886 845.

EP 0888769 discloses cosmetic compositions in a lyophilized form, containing 10 to 30% by wt alginates and 70 to 90% by wt. active substances, wherein plant extracts, algae extracts, minerals and trace elements as well as marine proteins, such as in particular marine collagens or marine nucleotides are specified as active substances. Active substances from the group of acid active substances are not being disclosed. Moreover, EP 0888769 also does not offer any suggestions as to a specific pH value of the compositions according to the invention, such as, in particular, a pH value <7 or even ≤6 or ≤4.

Therefore, a freeze-dried, mechanically stable, large-format active substance molded article was surprisingly obtained, which, due to the extremely low content in scaffold-forming agents according to the invention moreover could again be significantly improved with regard to its dissolution behavior as compared with the systems already known, such as those described in DE 10248314.

Moreover, it was surprisingly found that by selecting a scaffold-forming agent from the group of polyaminosaccharides, such as chitin or its derivatives, in particular by selecting chitosan as scaffold-forming agent, the stability and the dissolution behavior of such freeze-dried active substance molded articles with very low contents of scaffold-forming agents can be improved even further. This also applies to cationized starch derivatives or cationically modified carboxymethylcellulose.

To a large extent, this can be ascribed to the particularly good solubility of chitosan and cationized starch in acid pH ranges.

Neither DE 10248314 nor DE 2017373, nor any of the other documents discussed herein disclose a recipe with such low content of scaffold-forming agents, in particular selected from the group of chitin derivatives, such as chitosan or cationized starch or cationized carboxymethylcellulose and correspondingly high contents of active substances, in particular of acid, freezing-point lowering active substances, which can be incorporated by adjusting the pH value to pH ≤7, preferably pH ≤6, more preferably pH ≤5, particularly preferably pH ≤4, in order to arrive at porous, freeze-dried molded articles with the corresponding desired properties with regard to mechanical stability, dissolution behavior and size for the application in a cosmetic and pharmaceutical single-dosage application.

SUMMARY OF THE INVENTION

Thus, the invention provides freeze-dried molded articles comprising ≥50% by wt of one or more active substances and ≤15% by wt. of one or more scaffold-forming agent, with proteins being excepted, as well as optionally one or more auxiliary substances, in each case based on the total composition of the freeze-dried molded article, and whose 1% by wt. solution or suspension in water, at 20° C., has a pH value <7.

Furthermore, the invention provides a method for manufacturing these freeze-dried molded articles as well as the combination of such freeze-dried molded articles in kit-of-parts arrangements together with aqueous solutions, as well as the use of the freeze-dried molded articles and the kit-of-parts combinations for pharmaceutical and cosmetic application.

A molded article within the sense of the invention is understood to be a geometric body of a regular shape, for example, in particular, spheres, cuboids, pyramids, stars, but also molded articles replicating natural shapes, such as those in the form of animals, such as marine animals, such as starfishes, seafood, such as mussels, etc, plants and parts of plants, such as leaves etc. According to the method for producing the molded articles used according to the invention described below, all of these shapes are obtainable. Uniform spherical shapes are preferred according to the invention, such as, in particular, a spherical geometry, because it has shown itself to be particularly advantageous in particular with regard to the incorporation of large quantities of acid, freezing-point lowering active substances, such as ascorbic acid (vitamin C) and its derivatives or of acetylsalicylic acid and its derivatives, because of the particularly favorable ratio of surface area/volume. The sublimation distance through the already dry product is symmetric and small to all sides, which facilitates vapor transport through the already dry material within the context of the freeze-drying process.

DESCRIPTION OF PREFERRED EMBODIMENTS

In one aspect of the invention, a plurality of the molded articles mentioned are included in a container. This may also include mixtures of molded articles with different geometries or different sizes. The molded articles may be packaged individually, preferably, however, in particular in cosmetic application, a plurality of the molded articles lies in contact with each other next to each other in a container. The volumes of the molded articles used are not limited as such by the method of producing them. Expediently, the volumes are preferably about 0.1 cm$^3$, preferably 0.3 cm$^3$, more preferably at least about 0.5 cm$^3$, still more preferably at least about 0.6 cm$^3$. The upper limit of the volumes used is expediently about 6 cm$^3$, preferably about 5 cm$^3$, more preferably about 4 cm$^3$. Among other things, the size of the molded articles is determined by the desired form of application or the location of the external application of the molded articles. Thus, in external cosmetic or pharmaceutical use, the application to larger body surfaces or on the hair (e.g. direct application of the moistened molded articles on the back etc., or the use as a bath preparation) makes the use of larger molded articles possible, whereas smaller molded articles are preferred during use on smaller areas of the body (e.g. the cheek, etc.).

The size can also be adapted in the production of molded articles for oral application. For example, it is conceivable to adapt the size of the molded articles to the relevant target group, wherein it is conceivable that older users are offered larger molded articles that can be handled better, and to offer, for example, younger users and children such molded articles that have an adapted relationship to their body size and the compliance in application to be expected because of their age.

The diameter of a molded article (maximum distance between two points in a molded article of any geometry) expediently is at least about 3 mm, preferably at least about 5 mm, more preferably at least about 7 mm, still more preferably at least about 8 mm, up to, expediently, 60 mm, preferably about 50 mm, more preferably about 40 mm, still more preferably about 30 mm.

For the aforementioned reasons, a particularly preferred molded article has a substantially spherical geometry, with the diameter of the sphere being between 3 to 30 mm, preferably between 5 and 20 mm, more preferably between 7 and 15 mm, stiff more preferably between 8 and 14 mm. Molded articles in the shape of a sphere with a diameter of at least 6 mm are particularly preferred.

The freeze-dried molded articles according to the invention comprise at least one or more active substances, preferably at least one active substance in an amount of at least 50% by wt. or preferably even more than 50% by wt., based on the freeze-dried total composition. Active substances in particular include cosmetic or therapeutic or pharmaceutical active substances suitable for external use as well as for oral or peroral application. Preferably, the molded article used according to the invention comprises at least one cosmetic and/or pharmaceutical active substance. Accordingly, the freeze-dried molded articles according to the invention preferably are cosmetic or therapeutic products.

Cosmetic molded articles or molded articles produced using cosmetic active substances within the sense of the invention are substantially products within the sense of the German Food and Feed Code (LFGB), i.e. substances or preparations from substances that are intended for external application on humans for cleaning, care or influencing appearance or body odor, or for conveying olfactory impressions, unless they are primarily intended for alleviating or eliminating disease, disorders, bodily defects or pathological complaints. In this sense, the cosmetic molded articles used according to the invention are, for example, bathing preparations, skin washing and cleansing products, skin care products, in particular facial skin care products, eye cosmetics, lip care products, nail care products, foot care products, hair care products, in particular hair washing products, hair conditioning products, hair softening rinse etc., light protection products, suntan products and skin lightening products, depigmentation products, deodorants, antihydrotics, depilatory products, insect repellents etc, or a combination of such products.

Examples of cosmetically, or optionally, for example, dermatologically therapeutically effective substances can be: anti-acne products, antimicrobial products, antitranspiration products, astringent products, deodorizing products, depilatory products, conditioning products for the skin, skin-smoothing products, products for increasing skin hydration, such as glycerin or urea, sun blockers, keratolytic products, free-radical scavengers for free radicals, antiseborrhoeic products, anti dandruff products, antiseptic active substances, active substances for treating signs of the aging of the skin and/or products modulating the differentiation and/or proliferation and/or pigmentation of the skin, vitamins such as vitamin C (ascorbic acid) and its derivatives, e.g. glycosides such as ascorbyl glucoside or esters of ascorbic acid, such as sodium or magnesium ascorbyl phosphate or ascorbyl palmitate and stearate, L-ascorbic acid phosphate esters, alkaline metal salts, such as sodium and potassium salts of L-ascorbic acid phosphate esters; earth-alkaline metal salts such as magnesium and calcium salts of L-ascorbic acid phosphate esters; trivalent metal salts such as aluminum salts of L-ascorbic acid phosphate esters; alkaline metal salts, such as sodium and potassium salts of L-ascorbic acid sulfate esters; earth-alkaline metal salts such as magnesium and calcium salts of L-ascorbic acid sulfate esters; trivalent metal salts such as aluminum salts of L-ascorbic acid sulfate esters; alkaline metal salts, such as sodium and potassium salts of L-ascorbic acid esters; earth-alkaline metal salts such as magnesium and calcium salts of L-ascorbic acid esters; and trivalent metal salts such as aluminum salts of L-ascorbic acid esters.

Active substances with stimulating side-effects, such as alpha-hydroxy acids, β-hydroxy acids, alpha-keto acids, β-keto acids, retinoids (retinol, retinal, retinic acids), anthralins (dioxanthranol), anthranoids, peroxides (in particular benzoyl peroxide), minoxidil, lithium salts, antimetabolites, vitamin D and its derivatives, catechins, flavonoids, ceramides, polyunsaturated fatty acids, essential fatty acids (e.g. gamma-linolenic acid), enzymes, coenzymes, enzyme inhibitors, hydrating agents, skin-soothing agents, detergents or foam-forming agents, and inorganic or synthetic matting fillers, or decorative substances such as pigments or colorants and particles for foundations, make-up formulations, and other products for cosmetic beautification and coloring of the eyes, lips and face, as well as abrasive products.

Moreover, plant substance extracts or extracts obtained therefrom or individual substances can be mentioned. Generally, the plant active substance extract is regularly selected from the group consisting of solid plant extracts, liquid plant extracts, hydrophilic plant extracts, lipophilic plant extracts, individual plant ingredients and their mixtures, such as flavonoids and its aglycones: rutin, quercitin, diosmin, hyperoside, (neo)hesperidine, hesperitine, Ginkgo biloba (e.g. ginkgo flavone glycosides), Crataegus extract (e.g. oligomer procyanidines), buckwheat (e.g. rutin), Sophora japonica (e.g. rutin), birch leaves (e.g. quercitin glycosides, hyperoside and rutin), elderberry blossoms (e.g. rutin), lime blossom (e.g. essential oil with quercitin and farnesol), oil of St. John's wort (e.g. olive oil extract), calendula, arnica, (e.g. oily extracts of the blossoms with essential oil, polar extracts with flavonoids), melissa (e.g. flavones, essential oils), immunostimulants: Echinacea purpurea (e.g. alcoholic extracts, fresh plant juice, press-juice), Eleutherokokkus senticosus: alkaloids; Rauwolfia (e.g. Prajmalin), Vinca (e.g. vincamin); other phytopharmacons: Aloe, horse chestnut (e.g. aescine), garlic (e.g. garlic oil), pineapple (e.g. bromelaines) ginseng (e.g. ginsenosides), Silybum marianum fruits (e.g. extract standardized to silymarin), Butcher's broom wort (e.g. ruscogenin), valerian (e.g. valepotriates, Tct, Valerianae), Kava-Kava (e.g. kavalactone), hop (e.g. hop bitter substances). Extr. passiflorae, gentian (e.g. ethanolic extract), anthraquinone-containing drug extracts, e.g. aloin-containing aloe vera juice, pollen extract, algae extract, liquorice extracts, palm extracts, galphimia (e.g. mother tincture), mistletoe (e.g. aqueous-ethanolic extract), phytosterols (e.g. beta-sitosterin), common mulleins (e.g. aqueous-alcoholic extract), drosera (e.g. liqueur-wine extract), sea-buckthorn fruits (e.g. juice obtained therefrom or sea-buckthorn oil), marshmallow root, primrose-root extract, fresh plant extracts from mallow, comfrey, ivy, horsetail, yarrow, ribwort (e.g. pressed juice), stinging nettle, celandine, parsley; plant extracts from Norolaena lobata, Tagetes lucida, Teeoma siems, Momordica charantia and aloe-vera extracts.

Preferred cosmetic and pharmaceutical active substances include those that have a high instability with regard to decomposition or degradation, in particular as caused by the addition of moisture, and which, furthermore, generate an acid pH value in an aqueous solution due to acid groups in the active substance, so-called acid active substances. A particularly preferred active substance from the group of these unstable, acid and freezing-point lowering active substances, which is widely used in cosmetics, is ascorbic acid (vitamin C) and its derivatives, or also vitamin A and its derivatives.

In contrast to the above described molded articles, which are substantially used in cosmetics, the therapeutically used molded articles (medicaments) are such molded articles containing at least one pharmaceutical or therapeutic, in particular dermatologically active substance, and which, within the meaning of the "Arzneimittelgesetz" (German Medical Preparations Act), are intended to cure, to ease or to prevent diseases, illnesses, bodily damage or pathological complaints. Such agents or active substances are intended both for external use as well as oral or peroral application.

Active substances for external use are in particular skin-active, but also transdermal active substances. They include, for example: agents for the treatment of skin diseases, externally applicable analgesics, e.g. dextropropoxyphene, pentazocine, pethidine, buprenorphine; antirheumatics/antiphlogistics (NSAR), e.g. indomethacin, diclofenac, naproxen, ketoprofen, ibuprofen, flurbiprofen, salicylic acid and salicylic-acid derivatives such as acetylsalicylic acid, oxicams; steroid hormones, e.g. betamethasone, dexamethosone, methylprednisolone, ethynyl estradiol, medroergotamine, dihydroergotoxine; gout remedies, e.g. benzbromarone, allopurinol; external dermatological agents, including antibacterial agents, such as e.g. silver salts or colloidal silver, antimycotics, antiviral active substances, anti-inflammatory active substances, antipruritic active substances, anaesthetizing active substances, e.g. benzocaine, corticoids, anti-acne agents, antiparasitic active substances; externally applicable hormones: venous therapeutic agents; immunosuppressives etc., all for external application.

Preferred therapeutic products for external use are analgesics, e.g. immunosuppressives, hormones, products for the treatment of skin diseases such as neuredermitis, atopical dermatitis, acne, rosacea etc and anti-herpes products.

Therapeutic active substances for oral or peroral application can be selected from the group of antihistamines, antibiotics, peptide drugs, antimycotics, bronchial therapeutics such as antiasthmatics, antitussives, mucolytics, etc., antidiabetics, such as glibenclamide, hormones, steroid hormones, such as dexamethasone, cardiac glycosides such as digitoxin, heart and circulation therapeutics such as, e.g., beta blockers, antiarrhythmics, antihypertonics, calcium antagonists etc., psychopharmaceutical agents and antidepressants, such as tricyclic antidepressants (NSMRI), serotonin-specific reuptake inhibitors (SSRS), norepinephrine reuptake inhibitors (NRI), serotonin and norepinephrine reuptake inhibitors (SNRI), monoamino oxidase inhibitors (MAO inhibitors), etc., neuroleptics, anticonvulsives or antiepileptics, hypnotics, sedatives, anaesthetics, gastro-intestinal therapeutics, lipid-lowering drugs, analgesics, such as anti-migraine agents, paracetamol, salicylic acid and its derivatives such as acetylsalicylic acid, diclofenac, ibuprofen, ketoprofen, naproxen etc, antiphlogistics, vasodilators, diuretics, antipodagric agents, cytostatic agents, muscle relaxants, plant extracts, provitamins, such as beta carotene, vitamins such as vitamin C, A, B, E etc., silica, minerals and trace elements such as, e.g., potassium, magnesium, calcium, selenium, iodine, etc., dietary supplements and food supplements etc, all for oral and peroral application.

A particularly preferred pharmaceutical active substance which is used both for external as well as oral or peroral application and selected from the group of unstable, acid and freezing-point lowering substances is salicylic acid and its derivatives, such as acetylsalicylic acid (ASS). Other preferred unstable, acid and freezing-point lowering active substances are clofibric acid, ibuprofen, gemfibrozil, fenoprofen, naproxen, ketoprofen, indomethacin, bezafibrate, tolfenamine acid, diclofenac, meclofenamine acid, paracetamol, acitretine, acrivastine, azelaic acid, cromolyn, ethacrynic acid, furosemide, penicillin and derivatives thereof, risedronic acid and derivatives thereof, lipoic acid and ursodiol.

The freeze-dried molded articles according to the invention are characterized by a content of active substances of ≥50% by wt., preferably ≥75% by wt., more preferably ≥90% by wt., still more preferably ≥95% by wt., in each case based on the total composition of the freeze-dried molded articles. A content of active substances >50% by wt. is particularly preferred.

These are in particular such active substances which are selected from the group of the acid active substances, that is, active substances that generate an acid pH value in an aqueous solution due to acid groups in the active substance. Such acid active substances are in particular active substances whose 1% by wt. solution or suspension in water, at 20° C., has a pH value <7, or such active substances that have a pKa value, at 25° C., of ≤7.

The pKa value in this case denotes the negative decadic logarithm of the acid constant Ks. The acid constant is a material constant and furnishes information on the extent a substance (HA) reacts in an equilibrium reaction with water under protolysis.

$$HA + H_2O \rightleftharpoons H_3O^+ + A^-.$$

In this case, HA represents a Brønsted acid (after Brønsted), which can donate a proton $H^+$ to a solvent such as wafer, leaving behind an anion $A^-$. More generally, the Brønsted definition also applies to non-aqueous systems, in this case, the following applies for any protonable solvent Y:

$$HA + Y \rightleftharpoons HY^+ + A^-.$$

The acid constant Ks in this case denotes the equilibrium constant of this reaction and is a measure for the strength of an acid. The stronger the acid, the more the reaction is shifted towards the right side. This shows that, the smaller the pKs value, the stronger the acid.

Determination of the pKs value is carried out by measuring pH in a so-called half-titration. In the process, a solution of the acid of known concentration is provided and the pH value is measured, for example, by means of a pH measuring probe. Then, the acid is partially neutralized with a standard solution of a base of the same valence as the provided acid. In the process, exactly half of the substance quantity of the provided acid is added. The pH value is now determined again. The following applies:

$$pK_s = -lgK_s = -lg\frac{c[H^+] \cdot c[A^-]}{c[HA]}$$

Because after the addition of half of the substance quantity $c[A^-]=c[HA]$, pKs=pH applies for the so-called half-titration point.

Such acid active substances have a pH value-dependent high dissociation tendency, which is why the active substance is present in neutral to alkaline pH value ranges in a dissociated form and thus, in a high ion concentration. Such an increased ion concentration then results in a freezing-point lowering action with the aforementioned disadvantageous effects on the freeze-drying process, which is why such acid active substances could not be satisfactorily transferred into stable freeze-dried forms by freeze-drying processes, or only in very small concentrations or with very high cost expenditure by a process at very low temperatures with very long drying times.

In a preferred embodiment, the freeze-dried molded articles according to the invention, based on the total composition of the freeze-dried molded article, contain ≥50% by wt. of an active substance from the group of ascorbic acid and its derivatives.

In another preferred embodiment, the freeze-dried molded articles according to the invention, based on the total composition of the freeze-dried molded article, contain ≥50% by wt. of an active substance from the group of salicylic acid and its derivatives, preferably from the group of acetylsalicylic acid and its derivatives.

Thus, in particular such active substances can be generally subjected to freeze drying with the method according to the invention and the composition according to the invention, which, because of their pH value-dependent dissociation tendency, reduce the freezing point of water, in particular in high concentrations, and thus have a freezing-point lowering effect.

The term freezing-point lowering (or also meting-point lowering) denotes the phenomenon that the melting point of solutions is lower than that of the pure liquids.

For diluted solutions, the lowering of the freezing point ΔT is proportional to the molality n of the dissolved substance:

$$\Delta T = E_n \cdot n$$

In the process, the freezing point per mol of dissolved substance per kilogram solvent drops by a solvent-specific value. This value is called the cryoscopic constant En, which only depends on the solvent and not on the dissolved substance (in the case of water, this value is 1.86 (K·kg)/mol). It can be derived from Raoult's law and the Clausius-Clapeyron relation to $$E_n = R\frac{T_g^2}{L_S},$$

wherein
R is the general gas constant=8.314472 J/(mol·K),
Tg is the freezing point of the solvent in K, and
LS is the specific latent heat of the solvent in J/kg.

This relationship applies only for highly diluted solutions (concentration < 0.1 mol/L); in solutions of a higher concentration, the activity, and not the concentration of the ingredients and the water, must be taken into account.

It must be noted in this context that salts, acids and bases (electrolytes) dissociate in aqueous solutions. Consequently, because of this electrolytic dissociation, the lowering of the freezing point found is greater than might be expected based on the molar concentration.

In particular for active substances that exhibit electrolytic dissociation because of their acid active groups, such as ascorbic acid (vitamin C) and its derivatives, or salicylic acid and its derivatives, such as acetylsalicylic acid, stabilization against moisture can be made possible, even in high concentrations of active substances, in rapidly-soluble, large-format, mechanically stable freeze-dried molded articles, by means of the method according to the invention, which comprises the adjustment of the pH value of the active substance composition to a value of <7. Because of the chosen pH range, the acid-base equilibrium is shifted to the side of the acid, so that there are no dissociated ions present and the active substances are present in an electrically neutral form. Thus, the tendency to lower the freezing point is reduced, the problem of thawing of active substances with electrolytical dissociation tendency is counteracted, and highly concentrated active substance compositions can be freeze-dried without any loss of quality and stability of the molded articles. Moreover, the provision of active substance compositions in which the acid active substances are present in undissociated form is also preferred inasmuch as undissociated active substances, such as undissociated ascorbic acid, as such already have a better chemical stability, and moreover also have a better bioavailability during application.

Moreover, a freeze-dried molded articles composition with an acid pH value is advantageous because such acid compositions make an improved skin penetration of the active substances, which in this range of pH values are unloaded, possible in dermal and topical application.

Furthermore, acid freeze-dried molded articles, as was already explained, have a lower hygroscopic tendency because the protonated forms of the acid active substances act less hygroscopically than the unprotonated, dissociated active substances present in ionic form. One example, for an acid active substance in unprotonated form with an increased hygroscopic tendency that would have to be mentioned is, for example, sodium ascorbate.

Thus, the freeze-dried molded article according to the invention, in a 1% by wt. solution or suspension in water, at 20° C., has a pH value ≤7, preferably ≤pH 6.0, more preferably ≤pH 5.0, particularly preferably ≤pH 4.0. pH values <6 or <4 are particularly preferred.

The freeze-dried molded articles according to the invention moreover contain at least one scaffold-forming agent, with proteins being excepted, in an amount of ≤15% by wt., based on the total composition. The scaffold-forming agents generally are so-called hydrocolloids, i.e. (partially) water-soluble, natural or synthetic polymers that form gels or viscous solutions in aqueous systems. Expediently, the scaffold-forming agent are selected from polysaccharides, mucopolysaccharides, animal polyaminosaccharides such as chitin or its derivatives, in particular chitosan, or from the glucosaminoglycans as well as the synthetic polymers, such as in particular those of the group of the cationically modified starch or the cationically modified carboxymethylcellulose. Preferably, the scaffold-forming agent is selected from the group of polysaccharides. Polysaccharides include, for example, homoglycans or heteroglycans, such as, for instance, alginates, in particular sodium alginate, carrageen (herein also referred to under the English term "carrageenan"), pectins, gum tragacanth, guar gum, carob gum, agar-agar, gum arabic, pullulan, trehalose, xanthan gum, natural and modified, such as cationically modified starches, dextrans, dextrin, maltodextrins, glucans, such as β-1,3-glucan or β-1,4-glucan, such as cellulose, mucopolysaccharides, such as hyaluronic acid etc, as well as animal polyaminosaccharides, such as chitin or its derivatives, such as in particular chitosan. Synthetic polymers comprise, for example: cellulose ether, polyvinyl alcohol, polyvinyl pyrrolidone, synthetic cellulose derivatives, such as methylcellulose, carboxycellulose, carboxymethylcellulose, cationically modified carboxymethylcellulose, cellulose ester, cellulose ether such as hydroxypropylcellulose, polyacrylic acid, polymethacrylic acid, poly(methylmethacrylate) (PMMA), polymethacrylate (PMA), polyethylen glycols, etc. Mixtures of several scaffold-forming agents can also be used.

In a preferred embodiment, the freeze-dried molded articles according to the invention comprise at least one scaffold-forming agent selected from the group of the cationic scaffold-forming agents. Generally, these are understood to be those scaffold-forming agents that, under physiological environmental conditions (room temperature, neutral pH value range, aqueous environment) have more positive charges than negative charges on their surface.

In particular, cationically modified polymers comprise those in which at least one side group of the polymer skeleton is substituted by cationic groups. According to the invention, such cationically modified polymers are particularly preferred that have a degree of substitution (Sga) ≥1%. In this case, the degree of substitution, depending on the type of cationic group in the modified polymer, can be determined in accordance with the respectively suitable standard testing methods known to the person skilled in the art.

Generally, the term cationic polymers or scaffold-forming agent comprises in particular modified chitin derivatives, such as, in particular, chitosan, but also other chemically modified biopolymers, such as cationized celluloses (e.g. carboxymethylcellulose) or cationized starches.

Cationic biopolymers based on polysaccharides, such as celluloses or starches in this case comprise those in which some hydroxy groups in the polymer side chains are etherified with cationic groups or groups which, in an acid medium, can be converted into cationic groups by protonation. These substituents can consist, for example, of tertiary amino groups or quaternary ammonium salts, or also of sulfonium groups or phosphonium groups.

In a particularly preferred embodiment, the scaffold-forming agent is from the group of cationic scaffold-forming agent chitosan and/or cationically modified starch and/or cationically modified carboxymethylcellulose.

Other scaffold-forming agent that are particularly preferred according to the invention are hyaluronic acid and alginates, such as, in particular, sodium alginate.

The use of small quantities of scaffold-forming substances in the active-substance molded articles according to the invention as compared to, for example, pure, dried, additive-free active substances is necessary, on the one hand, in order to be able to provide the active substance in a suitable form of administration, which plays a role in particular in external use with regard to applicability and handling. In this case, in particular with regard to such active-substance molded articles to be applied externally, the scaffold-forming agent proportion is important for the texture formation of the rehydrated or dissolved active-substance molded article, so that the dissolved active substance can be applied well onto the skin or the hair. In contrast, purely aqueous active substance solutions would "run away" and, because of the lack of viscosity, are not feasible for external use for obvious reasons.

On the other hand, the scaffold-forming agent proportions, already in the small quantities according to the invention, make a decisive contribution with regard to the stability of the active-substance molded articles. Due to these already small quantities, the transfer of the active substances into a regular, uniform, geometric shape with a sufficient mechanical stability in packaging, storing, handling and use can be achieved. In particular, it was found, surprisingly, that the scaffold-forming agent contents according to the invention are already sufficient for providing non-dusting active substance molded articles that are sufficiently protected against mechanical abrasion.

The polysaccharides which, according to the invention, are preferably used as scaffold-forming agent, expediently have average molar masses of about $10^3$ to about $10^8$, preferably about $10^4$ to $10^7$.

The freeze-dried molded articles according to the invention are characterized in that they comprise a content of scaffold-forming agents of ≤15% by wt., preferably ≤10 by wt., more preferably ≤5 by wt., in each case based on the total composition of the freeze-dried molded article.

The scaffold-forming agent are skin- and mucosa-compatible, and have no toxicological potential, irritating effects or other incompatibility reactions, neither during external nor in the oral or peroral application. They are pharmacologically totally harmless and thus optimally suitable as carrier materials for the cosmetic and pharmaceutical external and oral or peroral uses according to the invention.

For clarification, it should also be mentioned that the wording "scaffold-forming agents, with proteins being excepted" within the sense of the invention does not exclude the presence of protein-based active substances, such as enzymes, hormones etc. These scaffold-forming agents, in particular polysaccharides, can also have certain therapeutic effects. Thus, the scaffold-forming agent (sodium) alginate, which is preferably used, to a certain extent has an antiviral action, and a certain action in re-epthelization and as an antioxidant and moisturizer in skin care is ascribed to hyaluronic acid; however, they are not active substances within the sense of the invention.

The molded articles used according to the invention furthermore optionally contain one or more auxiliary substances. Auxiliary substances include: pH-adjusting agents, buffering substances, inorganic and organic acids or bases, fatty substances, such as mineral oils, such as paraffin oils or Vaseline oils, silicone oils, vegetable oils such as coconut oil, sweet almond oil, apricot oil, corn oil, jojoba oil, olive oil, avocado oil, sesame oil, palm oil, eucalyptus oil, rosemary oil, lavender oil, pine oil, thyme oil, mint oil, cardamom oil, orange-blossom oil, soybean oil, bran oil, rice oil, rapeseed oil and castor oil, wheat-germ oil and vitamin E isolated therefrom, evening-primrose oil, vegetable lecithins (e.g. soybean lecithin), sphingolipids/ceramides isolated from plants, animal oils or fats, such as tallow, lanolin, butyric oil, fatty-acid esters, esters of fatty alcohols such as triglycerides, and waxes with a melting point corresponding to skin temperature (animal waxes such as beeswax, carnauba wax and candelilla wax, mineral waxes, such as microcrystalline waxes, and synthetic waxes, such as polyethylene waxes or silicone waxes), as well as ail oils that are suitable for cosmetic purposes (so-called cosmetic oils), such as, for example, those mentioned in the CFTA treatise entitled Cosmetic Ingredient Handbook, 1st edition, 1988. The Cosmetic, Toiletry and Fragrance Association, Inc., Washington, surfactants in addition to the above-mentioned washing tensides, such as dispersants, emulsifiers etc, fillers, stabilizers, cosolvents, pharmaceutically and cosmetically commonly used or other colorants and pigments, in particular those that are used primarily for the color design of the molded articles and not for application and color design on the human body, such as those pigments and colorants as those decorative colorants, preserving agents, softening agents, lubricants listed in the group of active agents.

A particularly preferred auxiliary agent is hydrochloric acid for adjusting the desired pH value of ≤7, preferably ≤6, more preferably ≤5, particularly preferably ≤4.

Furthermore, auxiliary substances from the group of fats and oils, in particular from the above-mentioned group of cosmetic oils, such as in particular jojoba oil, squalane or caprylic/capric acid triglycerides (neutral oil) are preferred. Other auxiliary substances preferred according to the invention are pH-regulating buffer substances and inert fillers.

Generally, the classification of the above-mentioned substances into the category of auxiliary substances within the context of the present invention does not preclude these auxiliary substances from also having certain cosmetic and/or therapeutic effects, which especially applies for the preferably used cosmetic oils mentioned.

Auxiliary substances can be added to the freeze-dried molded articles according to the invention in quantities of up to 25% by wt. based on the total composition.

The molded articles according to the invention serve for external cosmetic and pharmaceutical and oral or peroral use in humans and animals. External use is carried out such that the molded article according to the invention is moistened or dissolved with wafer or an aqueous solution containing one or more active substances and/or one or more auxiliary substances. Depending on the liquid quantity and the solubility of the material of the molded article used, the molded article can be dissolved completely while forming a solution, or decompose while forming a gel.

Preferably, aqueous solutions are used which in addition contain moisturizing alcohols, such as glycerin, butylene glycol or pentylene glycol, as well as those that have a low viscosity (a viscosity <50 mPas) and no or a merely low oil content (<10% by wt based on the total composition of the aqueous solution). Moreover, such activator solutions are preferred that are free from earth-alkaline ions, such as in particular calcium and/or magnesium ions (less than 1% by wt of calcium and/or magnesium ions based on the total composition of the aqueous solution contained), as well as those having a pH value of between about pH 4.0 to 8.0.

The solution of the molded article according to the invention in an amount of water suitable for a bathing application is also contained, according to the invention, in the external use. However, use is preferably carried out such that the molded articles are moistened with a small quantity of approximately 0.5 to 5.0 ml water or a solution of active substances and/or auxiliary substances while forming a solution or of a gel, directly on the skin or the hair or in a suitable container, decomposing there completely within ≤30 seconds. Preferably, the freeze-dried molded articles is dissolved with residue in the process. In this case, dissolution preferably takes place under slight mechanical influence, e.g. stirring, rubbing, squashing or massaging.

The present invention also relates to a combination comprising at least one of the molded articles used according to the invention, as well as at least one aqueous solution containing one or more active substances and/or at least one or more auxiliary substances (a so-called activator solution), in a combined spatial arrangement (application package, set, kit-of-parts etc.). The solutions of active substances can be, for example, solutions of highly volatile active and/or auxiliary substances, which should not or cannot be introduced into the molded article by freeze-drying because of the production process, such as certain parts of essential oils, perfumes, etc. Those active and/or auxiliary substances can also be contained which have a moisturizing effect which is desired and preferred in particular with regard to the external use on the skin, and which due to this moisturizing effect or due to hygroscopic tendencies cannot be incorporated into the freeze-dried molded article according to the invention, because thereby, the stability of the moisture-labile active substances cannot be maintained any longer.

The configuration of such kit-of-parts combinations of, on the one hand, molded articles according to the invention and the active substance solution, on the other hand, can provide that the two components are removed separately from the kit-of-parts arrangement and are combined and dissolved outside of it for further use. It is also conceivable, however, that a combination of the two components is carried out within the kit-of-parts packaging itself, and that the dissolved composition is then directly supplied from it to the further cosmetic or pharmaceutical external, oral and/or peroral use. Preferably, this can be done directly by the end user.

The molded articles according to the invention comprise at least 50% by wt. preferably 75% by wt. or more preferably 90% by wt. or more, still more preferably 95% by wt. or more of one or more active substances. Moisture-labile acid active substances are particularly preferred, in particular those with an electrolytic dissociation tendency and thus, a freezing-point lowering effect, such as, in particular, ascorbic acid (vitamin C) and its derivatives, and/or salicylic acid and its derivatives, such as acetylsalicylic acid (ASS).

The content of active substances in the dry total composition can be determined by suitable recognized analysis methods, such as according to DIN, Pharmacopeia, Amtliche Sammlung von Untersuchungverfahren (ASU, Official Collection of Testing Methods) etc. The choice of a suitable method is of course dependent upon the kind of active substance. In particular the particularly preferred active substances such as ascorbic acid (vitamin C) and its derivatives, and/or salicylic acid and its derivatives, such as acetylsalicylic acid (ASS) can be analyzed by high performance liquid chromatography methods (HPLC). HPLC methods for quantitative determination of vitamin C and acetylsalicylic acid can he taken from the official monographs "Aspirin Tablets" and "Ascorbic acid injections" from USP 31, NF 26 Volume 2, 2008, optionally with adaptation of the sample preparation.

Depending on the amount present and the type of the active substances present and/or possible additional auxiliary substances, the molded article according to the invention contains maximally about 15% by wt. of the scaffold-forming agent, based on the total weight of the freeze-dried molded article, preferably maximally or less than 10, more preferably maximally 7, still more preferably less than 5% by wt. of the scaffold-forming agent, in each case based on the total composition of the freeze-dried molded articles, with polysaccharides, such as sodium alginate or hyaluronic acid, or polyaminosaccharides, such as chitosan, or cationically modified polysaccharides, such as cationically modified starch or cationically modified carboxymethylcellulose, being particularly preferred.

The integral content of scaffold-forming agents in the dry total composition can in this case be determined by hydrolysis of the polymer chains present with a subsequent quantitative chromatographic defection of the individual monomer components. In the event this method cannot be used because of a special combination of different scaffold-forming agents and special active and auxiliary substances, the quantitative polymer content can be determined mathematically via the difference between the total weight and the quantitatively determinable auxiliary and active substances and water. The quantitative methods for determining the individual components of the recipe are borrowed from the official collections of methods already mentioned above.

The molded articles can contain up to about 25% by wt. of one or more auxiliary substances, preferably up to 10% by wt., more preferably less than 5% by wt. of one or more auxiliary substances, based on the total composition.

A preferred auxiliary substance is selected from the group of fats and oils, in particular from the group of cosmetic oils. They can be contained in the molded articles according to the invention in an amount of up to 50% by wt., more preferably 25% by wt.

Further preferred auxiliary substances are selected from the group of pH-adjusting agents, hydrochloric acid being particularly preferred in this case, which is optionally used for adjusting the pH value of the molded article compositions to pH≤7, preferably ≤6, more preferably ≤5, still more preferably ≤4. If the composition of active substances, scaffold-forming agent and optionally other auxiliary substances as such already has a pH value <7, which is desired according to the invention, then of course the addition of pH-adjusting agents be dispensed with.

Optionally, the molded articles also contain water residues. However, since the active substances contained in the molded articles, according to the invention, are to be stabilized particularly against moisture, the water content is to be kept as low as possible. Depending on the kind of active substance (hydrophilic, hydrophobic), the water content may be up to 10% by wt based on the total composition. The water content can change after the production of the molded article by freeze drying during storage; as a rule, it increases. Preferably, the water content of the molded article after its production is maximally 10% by wt., preferably less than 5% by wt., more preferably less than 1% by wt., with it having been found, surprisingly, that, due to the method according to the invention for producing the molded articles according to the invention, which includes as an essential feature of the invention the adjustment of the pH value of the composition to a pH value ≤7, preferably ≤6, more preferably ≤5, still more preferably ≤4, the residual moisture can be significantly reduced during the drying of the molded articles as compared to known molded articles, which are produced without such a step of adjusting the pH value, as disclosed, for example, in DE 10248314. Due to the lower residual moisture of the molded articles caused by production, an additional stabilization of the active substances can be achieved.

A particularly preferred molded article comprises:
- ≥50% by wt of one or more active substances, in particular acid active substances, such as ascorbic acid (vitamin C) or its derivatives, or salicylic acid or its derivatives, such as acetylsalicylic acid (ASS)
- ≤15% by wt. of one or more scaffold-forming agents, preferably low-viscosity scaffold-forming agent, in particular polysaccharides, such as hyaluronic acid and/or sodium alginate, in particular calcium-free sodium alginate, or cationic scaffold-forming agents, such as in particular chitosan from the group of polyaminosaccharides, or cationically modified polysaccharides, such as cationized starch or cationized carboxymethylcellulose.
- ≤25% by wt of one or more auxiliary substances, such as, in particular, cosmetic oils as well as pH-adjusting agents, such as hydrochloric acid, and
- up to 10% by wt., preferably up to 5% by wt., more preferably less than 1% by wt. of water, with the condition that the molded article comprises no proteins as scaffold-forming agents, and that their 1% by wt. solution or suspension in water, at 20° C., has a pH value <7.

Preferably, the molded article used according to the invention, such as that of the above-mentioned composition, comprising at least 50% by wt of one or more active substances and maximally 15% by wt. of one or more scaffold-forming agents, with proteins being excepted, has
- a pH value ≤6, more preferably ≤5, still more preferably ≤4, measured in its 1% by wt. solution or suspension in water at 20° C.,
- a density of 0.005 g/cm$^3$ to 0.8 g/cm$^3$ preferably 0.01 g/cm$^3$ to 0.8 g/cm$^3$,
- a volume of 0.1 cm$^3$ to 6 cm$^3$, preferably 0.8 cm$^3$ to 6 cm$^3$,
- a diameter (maximum distance between two points of the molded article) of at least 6 mm, and/or
- preferably a spherical configuration, particularly preferably the shape of a sphere.

The molded articles according to the invention constitute porous molded articles with a homogeneous distribution of the ingredients (with the exception of optionally present coatings).

The molded articles according to the invention, such as, for example, those as mentioned above, are preferably dissolved with an aqueous liquid/activator solution, which comprises:
- at least 70% by wt. of water,
- at least 5% by wt. of polyalcohols,
- up to 10% by wt. of one or more active substances, such as, in particular, those from the group of the cosmetic active substances
- up to 20% by wt. of one or more auxiliary substances, such as in particular those from the group of cosmetic oils, such as in particular caprylic/capric acid triglycerides and suitable emulsifiers, and which has a pH value of 5-7 and, furthermore, a content of earth-alkaline ions, such as, in particular, calcium and/or magnesium ions of less than 1% by wt.

The dissolution rate of the molded articles used according to the invention, measured in accordance with a method for measuring the "disintegration time of tablets and capsules" with a testing apparatus according to PharmEU is less than 30 seconds, still more preferably less than 20 seconds (in the case of molded articles with a diameter of 11 mm, there is complete hydration without recognizable core after <10 seconds).

The molded articles according to the invention can be obtained by a method comprising the following steps:
(a) preparing an aqueous solution or suspension comprising one or more scaffold-forming agents, with proteins being excepted, one or more active substances, as well as one or more auxiliary substances,
(b) optionally adjusting the pH value of this aqueous solution or suspension to pH<7,
(c) pouring the mixture into a mold,
(d) freezing the mixture in the mold, and
(e) freeze drying the frozen mixture while forming the molded article.

Preferably, the pH value of the aqueous solution or suspension is adjusted in step (b) to a pH value of <6, still more preferably to a pH value <4.

Optionally, other steps can be carried out between these steps; in particular, it is possible to remove the frozen molded article from the mold after step (d). Moreover, it is possible to then carry out a processing of the surface of the frozen molded articles by mechanical processing or by application or spraying with, for example, active substance solutions, colorant solutions, and/or agents modifying the dissolution rate. Preferably, however, the molded article does not have a surface coating and is homogeneously configured, in the sense of the components being distributed equally over the entire molded article.

Expediently, the production is carried out by first preparing an aqueous solution of the scaffold-forming agent and subsequently adding and mixing in the active substance(s) as well as optionally one or more auxiliary substances. Optionally, after mixing all of the constituents, the desired pH value is adjusted to ≤7, preferably <6, more preferably ≤5, still more preferably ≤4, optionally by adding the auxiliary substances from the group of pH-adjusting agents.

In order to provide the molded article with a sufficient mechanical stability, it is necessary for the solution or suspension to have a certain concentration of the scaffold-forming agent, which, however, according to the invention is maximally 15% by wt. based on the freeze-dried total composition. The respective exact concentration of course depends on the type of scaffold-forming agent used. Expediently, it is about at least 0.3% by wt. based on the total quantity of the solution, preferably at least about 0.5% by wt. to about 1.0% by wt., preferably less than 3.0% by wt., still more preferably less than 1.5% by wt. (weight of the scaffold-forming agent based on the total weight of the solution).

The amount of the solids contained in the solution or suspension, such as scaffold-forming agents, active substances and auxiliary substances is an important influence on the density (weight of the molded article relative to the volume of the geometrical form of the molded article) of the molded article obtained. The density in turn is an important quantity for the porosity of the molded article, and thus for the dissolution rate of the molded article when moistened with water or a solution of active and/or auxiliary substances. The porous structure of freeze-dried molded articles is an essential basis for rapid solubility because an intimate exchange between the aqueous phase and the solid molded article can occur during the rehydration process due to the large surface area in the porous material. The higher the concentration of the active substances, of the scaffold-forming agent as well as of, optionally, the auxiliary substances in the solution, the higher the density becomes, and thus, the lower the degree of porosity of the molded article and vice versa. However, the degree of porosity of the molded articles does not depend on the material density alone. Rather, material porosity is substantially a function of two parameters, the material density and the ice-crystal size. High solid contents in the aqueous suspension increase material density in the freeze-dried final product and reduce the contact surface between the rehydration agent/solid. Large freezing gradients lead to small ice crystals, which lead to large internal material surfaces, which in turn promotes rehydration. Thus, small material densities and small ice crystals are advantageous for quick moisturization and dissolution of the freeze-dried molded articles.

If high concentrations of active substances that lower the freezing point of water due to their electrolytic dissociation, such as ascorbic acid (vitamin C) or acetylsalicylic acid, are now used in the emulsion, then large ice crystals form as a rule, and general problems in the freezing process arise. A large content of unfreezable water with high concentrations of active substances results, which consequently leads to a partial structural collapse of the freeze-dried final product during freeze-drying. The molded article "thaws".

With regard to density/degree of porosity and dissolution rate, respectively, the formulation of the recipe and the production of the molded articles according to the invention is arranged such that the densities of the molded articles that can be obtained therewith are expediently about 0.01 g/cm$^3$ to 0.8 g/cm$^3$, preferably about 0.015 g/cm$^3$ to 0.5 g/cm$^3$, preferably about 0.02 g/cm$^3$ to 0.25 g/cm$^3$. The term density as it is presently used denotes the weight of the molded article relative to the volume of the exterior geometric shape of the composition.

The weight of the individual molded articles is of course dependent upon their size. Generally, the weight of the individual molded articles is about 10 to 300 mg, preferably 20 to 200 mg. For example, spheres with a diameter of 11 mm have a weight in the range from, preferably, 20 to 150 mg, more preferably 50 to 125 mg. Corresponding preferred ranges are calculated for spheres having other diameters.

With regard to ice-crystal formation/degree of porosity, it was found, surprisingly, that the thawing problems and the accompanying formation of large ice crystals with a high content of unfreezable water during the incorporation of high concentration of active substances of, in particular, acid active substances with dissociable acid-base groups can be solved by, on the one hand, adjusting the pH value to a pH ≤7, preferably ≤6, more preferably ≤5, still more preferably ≤4, in order to shift the acid-base equilibrium in favor of the undissociated acid, and, on the other hand, by the selection of a freezing geometry in which the molded article is frozen in simultaneously from all sides at at least <−20° C. This method, freezing within a mold, for example by blowing with cold air, reduced the proportion of non-thawable water to a minimum, so that subsequently, drying may take place at higher temperatures, which in turn reduces the costs for the freeze-drying process considerably. In addition, a spherical configuration, such as, in particular, a sphere geometry, is beneficial for drying the molded articles with high contents of active substances, because, due to the beneficial surface area/volume ration of the spherical shape, the sublimation through the product is symmetrical towards all sides and directed to small distances, which in turn facilitates vapor transport during sublimation.

The solution that is subjected to freeze drying is preferably prepared such that a solution of the scaffold-forming agent is prepared first, and the active substances or auxiliary substances possibly present are then incorporated into the solution of the scaffold-forming agent. If oil-soluble active substances are used, they are preferably dissolved in oils that are optionally used as auxiliary substances (in particular squalane, jojoba oil and triglycerides) and then added to the solution of the scaffold-forming agent. This production method is advantageous in that stable solutions or suspensions form in a short time. No or only small amounts of emulsifiers or surfactants, such as tensides, are required, and no phase separation of the solution or suspension occurs during processing if oil-soluble or oily auxiliary or active substances are used. Preferably, however, water-soluble active substances are used.

The solution or suspension thus produced is then poured into molds which have cavities of the desired geometric shapes corresponding to the molded articles. The mold preferably consists of rubber, silicone rubber, vulcanized rubber (rubber) etc. Rubber molds are preferred. The mold materials may optionally be coated. The cavities of the molded articles into which the solution is poured generally have the shape of the desired molded article. That is, the volume of the cavity substantially corresponds to the volume of the molded article that is obtained later.

Since the volume of the solutions or suspensions filled in the cavities increases during freezing (difference in density between water and ice), the cavities are generally not filled completely. In this way, completely symmetrical molded articles are obtained. For example, this is not possible according to the method of dripping into cryogenic solutions (such as in liquid nitrogen), because in that case, unsymmetrical temperature distribution occurs, so that greater or lesser deviations from a regular form result every time. Such irregularly shaped molded articles, however, are not desired especially in the area of cosmetic final products. As a rule, this means that molded articles produced according to the dripping method require mechanical post-processing, which is not necessary according to the method as it is used according to the invention. In the case of molded articles produced with the dripping method, such post-processing becomes ever more necessary with an increasing volume of the molded article, because significant external irregularities occur in this method, which become more apparent in the case of large molded articles.

After the solution has been filled into the cavities of the mold, the solution or suspension is frozen. Cooling or freezing the solution can take place, as such, in any way, such as, for example, by blowing with cold air, cooling by applying on a plate through which cooling brine flows, or also dipping the molds into liquid gases, such as dipping into liquid nitrogen. The cooling rate in the process has an effect upon the size of the ice crystals formed. They in turn have an effect upon the pore size distribution of the molded article formed. If few large crystals are formed, then the molded article exhibits few large pores, which is not desired for the above-mentioned reasons, namely thawing problems during the incorporation of large concentrations of freezing-point lowering active substances. If many small crystals are formed, then the molded article has many small pores. The higher the cooling-off rate of the solution or suspension, the smaller the crystals become. As was already explained, freezing geometries in which the molded articles are frozen simultaneously from all sides at at least <−20° C. are preferred.

The freezing temperature required depends, among other things, on how large the freezing-point lowering action of the active agents or auxiliary substances contained in the solution or suspension is. Expediently, the temperature is below the freezing point of water, down to the temperature of liquid nitrogen (−196° C.). Preferably, the freezing temperature is about −20° C. to −80° C., preferably −25° C. to −45° C. After the solution or suspension has frozen, the molded articles are removed from the mold and subjected to post-processing, if necessary. Post-processing can take place mechanically, e.g., by surface processing (grinding, roughening). Moreover, a coating treatment is possible, such as spraying with a salt solution, e.g. for forming less soluble forms of the scaffold-forming agents, in particular in case of use of sodium alginate and salt solutions of multivalent metal ions. Moreover, a colored solution can be superficially applied on the frozen molded articles, which results in colored molded articles.

The molded articles are then subjected to the freeze-drying process. Freeze drying can take place in a manner known per se, according to generally known freeze-drying processes such as also described, for example, in DE 4328329 C2, in DE 4028622 C2 or in DE 10350654 A1.

The invention in particular includes the following preferred embodiments:

1. Freeze-dried molded article, characterized in that if comprises ≤50% by wt. of one or more active substances and ≥15% by wt. of one or more scaffold-forming agents, with proteins being excepted, as well as optionally one or more auxiliary substances, in each case based on the total composition of the freeze-dried molded article, and whose 1% by wt. solution or suspension in water, at 20° C., has a pH value <7.
2. Freeze-dried molded article according to embodiment 1, comprising a content of active substances of ≤75% by wt., more preferably ≥90% by wt., still more preferably ≥95% by wt., in each case based on the total composition of the freeze-dried molded article.
3. Freeze-dried molded article according to any one of the embodiments 1 or 2, wherein a 1% by wt. solution or suspension of the active substance in water, at 20° C., has a pH value <7.
4. Freeze-dried molded article according to any one of the embodiments 1 to 3, wherein the active substance is selected from the group of acid active substances having a pKa value ≤7 at 25° C.
5. Freeze-dried molded article according to any one of the embodiments 1 to 4, wherein the active substance is selected from the group consisting of ascorbic acid and its derivatives, and salicylic acid and its derivatives, in particular acetylsalicylic acid, clofibric acid, ibuprofen, gemfibrozil, fenoprofen, naproxen, ketoprofen, indomethacin, bezafibrate, tolfenamine acid, diclofenac, meclofenamine acid, paracetamol, acitretine, acrivastine, azelaic acid, cromolyn, ethacrynic acid, furosemide, penicillin and derivatives thereof, vitamin A and derivatives thereof, risedronic acid and derivatives thereof, lipoic acid and ursodiol.
6. Freeze-dried molded article according to any one of the embodiments 1 to 5, which, based on the total composition of the freeze-dried molded article, contains ≥50% by wt. of an active substance from the group of ascorbic acid and its derivatives.
7. Freeze-dried molded article according to any one of the embodiments 1 to 5, which, based on the total composition of the freeze-dried molded article, contains ≥50% by wt. of an active substance from the group of salicylic acid and its derivatives, preferably from the group of acetylsalicylic acid and its derivatives.

8. Freeze-dried molded article according to any one of the embodiments 1 to 7, with a content of scaffold-forming agents of ≤10% by wt., more preferably ≤5% by wt., in each case based on the total composition of the freeze-dried molded article.
9. Freeze-dried molded article according to any one of the embodiments 1 to 8, wherein the scaffold-forming agents are selected from the group of the polysaccharides, polyaminosaccharides, glucosaminoglycanes and/or synthetic polymers or mixtures thereof, preferably from the group of polysaccharides and polyaminosaccharides.
10. Freeze-dried molded article according to embodiment 9, wherein at least one scaffold-forming agent is selected from the group of the cationic scaffold-forming agents.
11. Freeze-dried molded article according to any one of the embodiments 1 to 10, wherein at least one scaffold-forming agent is chitosan and/or cationized starch and/or cationized carboxymethylcellulose.
12. Freeze-dried molded article according to any one of the embodiments 1 to 9, wherein at least one scaffold-forming agent is selected from the group of the alginates, preferably from the group of sodium alginates.
13. Freeze-dried molded article according to any one of the embodiments 1 to 12, whose 1% by wt. solution or suspension in water, at 20° C., has a pH value ≤pH 6.0, preferably ≤pH 5.0, more preferably ≤pH 4.0.
14. Freeze-dried molded article according to any one of the embodiments 1 to 13, whose 1% by wt. solution or suspension in water, at 20° C., has a pH value <pH 6.0, and wherein the active substance is selected from the group of acid active substances having a pKa value ≤7 at 25° C.
15. Freeze-dried molded article according to any one of the embodiments 1 to 14, whose 1% by wt. solution or suspension in water, at 20° C., has a pH value <pH 4.0, and wherein the active substance is selected from the group of acid active substances having a pKa value ≤7 at 25° C.
16. Freeze-dried molded article according to any one of the embodiments 1 to 13, with a content of scaffold-forming agents of <15% by wt., based on the total composition of the freeze-dried molded article, and wherein the active substance is selected from the group of acid active substances having a pKa value ≤7 at 25° C.
17. Freeze-dried melded article according to any one of the embodiments 1 to 16, which decomposes completely within ≤30 seconds when liquid is added.
18. Freeze-dried molded article according to any one of the embodiments 1 to 17, which has a volume of 0.1 cm$^3$ to 6 cm$^3$, a density of 0.01 g/cm$^3$ to 0.8 g/cm$^3$ and/or the geometrical shape of a sphere with a diameter of at least 6 mm.
19. Method for producing a freeze-dried molded article according to any one of the embodiments 1 to 18, comprising the following steps:
    (a) preparing an aqueous solution or suspension comprising one or more scaffold-forming agents, with proteins being excepted, one or more active substances, as well as one or more auxiliary substances,
    (b) optionally adjusting the pH value of this aqueous solution or suspension to pH<7,
    (c) pouring the mixture into a mold,
    (d) freezing the mixture in the mold, and
    (e) freeze drying the frozen mixture while forming the molded article.
20. Method according to embodiment 19, wherein the frozen mixture from step (d) is taken out of the mold prior to the freeze drying according to step (e).
21. Method according to any one of the embodiments 19 or 20, wherein the pH value is adjusted to pH<6, preferably to pH<4, in step (b).
22. Freeze-dried molded article that can be obtained in accordance with the method according to any of the embodiments 19 to 21.
23. Use of the freeze-dried molded article according to any one of the embodiments 1 to 18 or 22 as a cosmetic agent.
24. Use of the freeze-dried molded article according to any one of the embodiments 1 to 18 or 22 as a pharmaceutical agent.
25. Use according to embodiment 23 or 24, wherein the application takes place externally.
28. Use according to any one of the embodiments 23 to 25, wherein the freeze-dried molded article is moistened with water or an aqueous solution of one or more active substances and/or, optionally, auxiliary substances and decomposes and is then applied onto the skin or hair.
27. Use of the freeze-dried molded article according to any one of the embodiments 1 to 18 or 22 for the oral or peroral application of active substances.
28. Kit-of-parts combination, comprising at least one freeze-dried molded article according to any one of the embodiments 1 to 18 or 22, as well as at least one aqueous solution comprising one or more active substances and/or, optionally, one or more auxiliary substances, in a combined spatial arrangement.
29. Use of the kit-of-parts combination according to embodiment 28 as a cosmetic agent.
30. Use of the kit-of-parts combination according to embodiment 28 as a therapeutic agent.
31. Use according to any one of the embodiments 23 to 27 and 29 to 30, which is carried out directly by the end user.

Furthermore, the invention is illustrated in more detail by the following examples.

EXAMPLES

Example 1

Ascorbic Acid Sphere, Diameter 11 mm

Ascorbic Acid with Hyaluronic Acid

| | |
|---|---|
| 1.0 g | hyaluronic acid |
| 16.0 g | ascorbic acid |
| 83.0 g | water |

1.0 g hyaluronic acid are added to 83.0 g water with stirring, and mixed homogeneously. 16.0 g ascorbic acid are then added with stirring, the mixture, which has a pH value of ≤3.0, is kept at a temperature of 0-10° C. in the process. The homogeneous (degassed) mixture is poured into molds, frozen through with air blowing, taken out of the mold and subsequently freeze-dried in a manner known per se.
The freeze-dried molded article contains:
94.1% by wt. ascorbic acid
5.9% by wt. hyaluronic acid
The dissolution rate of the freeze-dried molded articles, measured in accordance with a method for measuring the "disintegration time of tablets and capsules" with a testing apparatus according to PharmEU, is less than 10 seconds.

Example 2

Ascorbic Acid Sphere, Diameter 11 mm

A mixture as in example 1 is adjusted to pH 3.0 with diluted sodium hydroxide solution (0.1 mol/L) prior to being filled into molds.

The dissolution rate of the freeze-dried molded articles, measured in accordance with a method for measuring the "disintegration time of tablets and capsules" with a testing apparatus according to PharmEU, is less than 5 seconds.

Example 3

Ascorbic Acid Sphere, Diameter 13 mm

Ascorbic Acid with Chitosan

| | |
|---|---|
| 0.9 g | chitosan |
| 17.6 g | ascorbic acid |
| 81.5 g | water |

0.9 g chitosan are added to 81.5 g water with stirring, and mixed homogeneously. The chitosan is dissolved by adding concentrated hydrochloric acid, and a pH value of 3.0 is set after the dissolution of the chitosan. 17.6 g ascorbic acid are then added with stirring, the mixture, which has a pH value of <3, is kept at a temperature of 0-10° C. in the process. The homogeneous (degassed) mixture is poured into molds, frozen through with air blowing, taken out of the mold and subsequently freeze-dried in a manner known per se.

The freeze-dried molded article contains;
95.1% by wt. ascorbic acid
4.8% by wt. chitosan The dissolution rate of the freeze-dried molded articles, measured in accordance with a method for measuring, the "disintegration time of tablets and capsules" with a testing apparatus according to PharmEU, is less than 10 seconds.

Example 4

Ascorbic Acid Sphere, Diameter 13 mm

A mixture as in example 3 is adjusted to pH 3 with diluted sodium hydroxide solution (0.1 mol/L) prior to being filled into molds.

The dissolution rate of the freeze-dried molded articles, measured in accordance with a method for measuring the "disintegration time of tablets and capsules" with a testing apparatus according to PharmEU, is less than 10 seconds.

Example 5

Ascorbic Acid Sphere with Alginate+Carboxymethylcellulose+Hyaluronic Acid, Diameter 15 mm

| | |
|---|---|
| 0.5 g | sodium alginate |
| 0.5 g | sodium hyaluronate |
| 0.5 g | sodium carboxymethylcellulose |
| 9.0 g | ascorbic acid |
| 89.5 g | water |

0.5 g sodium alginate, 0.5 g sodium hyaluronate and 0.5 g sodium carboxymethylcellulose are added to 89.5 g water with stirring, and mixed homogeneously 9.0 g ascorbic acid are then added with stirring, the mixture, which has a pH value of <3, is kept at a temperature of 0-10° C. in the process. The homogeneous (degassed) mixture is poured into molds, frozen through with air blowing, taken out of the mold and subsequently freeze-dried in a manner known per se.

The freeze-dried molded article contains;
85.7% by wt. ascorbic acid
4.8% by wt. hyaluronic acid
4.8% by wt. sodium alginate
4.8% by wt. sodium carboxymethylcellulose The dissolution rate of the freeze-dried molded articles, measured in accordance with a method for measuring the "disintegration time of tablets and capsules" with a testing apparatus according to PharmEU, is less than 10 seconds.

Example 6

Acetylsalicylic Acid with Alginate, Diameter 9 mm

| | |
|---|---|
| 0.8 g | sodium alginate |
| 0.3 g | carrageenan |
| 5.0 g | neutral oil |
| 4.0 g | PEG-40 hydrogenated castor oil |
| 13.0 g | acetylsalicylic acid |
| 76.9 g | water |

0.8 g sodium alginate, 0.3 g carragenan are added to 76.9 g water with stirring, and mixed homogeneously. 13 g acetylsalicylic acid are slurried in 5 g neutral oil and 4 g PEG-40 hydrogenated castor oil. The slurry is added to the alginate-carrageenan suspension with stirring. The mixture is then adjusted to a pH value <3 with diluted hydrochloric acid. The homogeneous (degassed) mixture is poured into molds, frozen through with air blowing, taken out of the mold and subsequently freeze-dried in a manner known per se.

The freeze-dried molded article contains:

| | |
|---|---|
| 56.3% | acetylsalicylic acid |
| 21.6% | neutral oil |
| 17.3% | PEG-40 hydrogenated castor oil |
| 3.5% | sodium alginate |
| 1.3% | carrageenan |

The dissolution rate of the freeze-dried molded articles, measured in accordance with a method for measuring the "disintegration time of tablets and capsules" with a testing apparatus according to PharmEU, is less than 10 seconds.

Example 7

Acetylsalicylic Acid Sphere with Chitosan, Diameter 9 mm

| | |
|---|---|
| 1.0 g | chitosan |
| 5.0 g | neutral oil |
| 4.0 g | PEG-40 hydrogenated castor oil |
| 13.0 g | acetylsalicylic acid |
| 77.0 g | water |

1.0 g chitosan is added to 77.0 g water with stirring while adding concentrated hydrochloric acid and dissolved. The chitosan solution is brought to a pH value of 3.0. 13 g acetylsalicylic acid are slurried in 5 g neutral oil and 4 g PEG-40 hydrogenated castor oil. The slurry is added to the chitosan suspension with stirring. The mixture is then adjusted to a pH value ≤3 with diluted hydrochloric acid. The homogeneous (degassed) mixture is poured into molds, frozen through with air blowing, taken out of the mold and subsequently freeze-dried in a manner known per se.

The freeze-dried molded article contains:

| | |
|---|---|
| 56.5% | acetylsalicylic acid |
| 21.8% | neutral oil |
| 17.4% | PEG-40 hydrogenated castor oil |
| 4.3% | chitosan |

The dissolution rate of the freeze-dried molded articles, measured in accordance with a method for measuring the "disintegration time of tablets and capsules" with a testing apparatus according to PharmEU, is less than 5 seconds.

Example 8

Ascorbic Acid Sphere+Cationized Starch, Diameter 11 mm

Ascorbic Acid with Cationized Starch

| | |
|---|---|
| 2.0 g | cationized starch |
| 16.0 g | ascorbic acid |
| 82.0 g | water |

2.0 g cationized starch are added to 82.0 g water with stirring, and mixed homogeneously. 16.0 g ascorbic acid are then added with stirring, the mixture, which has a pH value of ≤3.0, is kept at a temperature of 0-10° C. in the process. The homogeneous (degassed) mixture is poured into molds, frozen through with air blowing, taken out of the mold and subsequently freeze-dried in a manner known per se.

The freeze-dried molded article contains:
11.1% by wt. cationized starch
88.9% by wt. ascorbic acid The dissolution rate of the freeze-dried molded articles, measured in accordance with a method for measuring the "disintegration time of tablets and capsules" with a testing apparatus according to PharmEU, is less than 5 seconds.

The invention claimed is:

1. Freeze-dried molded article, comprising <50% by wt. of one or more active substances selected from the group of acid active substances having a pKa value < or equal to 7 at 25° C., and
    ≤15% by wt. of one or more scaffold-forming agents, with proteins being excepted,
    as well as optionally one or more auxiliary substances, in each case based on the total composition of the freeze-dried molded article, and whose 1% by wt. solution or suspension in water, at 20° C., has a pH value <7.

2. Freeze-dried molded article according to claim 1, comprising a content of acid active substances of ≥75% by wt., based on the total composition of the freeze-dried molded article.

3. Freeze-dried molded article according to claim 1, which, based on the total composition of the freeze-dried molded article, contains >50% by wt. of an active substance from the group of ascorbic acid and its derivatives or the group of salicylic acid and its derivatives.

4. Freeze-dried molded article according to claim 1, with a content of scaffold-forming agents of <10% by wt. based on the total composition of the freeze-dried molded article.

5. Freeze-dried molded article according to claim 1, wherein the scaffold-forming agents are selected from the group of the polysaccharides, polyaminosaccharides, glucosaminoglycanes and/or synthetic polymers or mixtures thereof.

6. Freeze-dried molded article according to claim 1, whose 1% by wt. solution or suspension in water, at 20° C, has a pH value <pH 4.0.

7. Freeze-dried molded article according to claim 1, which decomposes completely within ≤30 seconds when liquid is added.

8. Method for producing a freeze-dried molded article according to claim 1, comprising the following steps:
    (a) preparing an aqueous solution or suspension comprising one or more scaffold-forming agents, with proteins being excepted, one or more active substances, as well as one or more auxiliary substances,
    (b) optionally adjusting the pH value of this aqueous solution or suspension to pH <7,
    (c) pouring the mixture into a mold,
    (d) freezing the mixture in the mold, and
    (e) freeze drying the frozen mixture while forming the molded article.

9. Freeze-dried molded article that can be obtained in accordance with the method according to claim 8.

10. Freeze-dried molded article according to claim 9, which, based on the total composition of the freeze-dried molded article, contains >50 % by wt. of an active substance from the group of ascorbic acid and its derivatives or the group of salicylic acid and its derivatives.

11. Freeze-dried molded article according to claim 2, which, based on the total composition of the freeze-dried molded article, contains >50% by wt. of an active substance from the group of ascorbic acid and its derivatives or the group of salicylic acid and its derivatives.

12. Freeze-dried molded article according to claim 10, with a content of scaffold-forming agents of <10% by wt. based on the total composition of the freeze-dried molded article.

* * * * *

UNITED STATES PATENT AND TRADEMARK OFFICE
CERTIFICATE OF CORRECTION

| | | |
|---|---|---|
| PATENT NO. | : 9,023,369 B2 | |
| APPLICATION NO. | : 12/763605 | |
| DATED | : May 5, 2015 | |
| INVENTOR(S) | : Ralf Malessa et al. | |

It is certified that error appears in the above-identified patent and that said Letters Patent is hereby corrected as shown below:

In the Claims

In Claim 1, Column 29, Line 48, replace "<50% by wt" with -- >50% by wt --.

Signed and Sealed this
Twenty-sixth Day of December, 2023

Katherine Kelly Vidal
Director of the United States Patent and Trademark Office